US006254890B1

(12) United States Patent
Hirosue et al.

(10) Patent No.: US 6,254,890 B1
(45) Date of Patent: Jul. 3, 2001

(54) SUB-100NM BIODEGRADABLE POLYMER SPHERES CAPABLE OF TRANSPORTING AND RELEASING NUCLEIC ACIDS

(75) Inventors: Sachiko Hirosue, Cambridge, MA (US); Bernhard G. Mueller, Kaltbach (CH); Robert S. Langer, Newton, MA (US); Richard C. Mulligan, Lincoln, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/209,031

(22) Filed: Dec. 10, 1998

Related U.S. Application Data

(60) Provisional application No. 60/069,360, filed on Dec. 12, 1997.

(51) Int. Cl.[7] .............................. A61K 9/51; A61K 9/52; A61K 9/64; A61K 9/58
(52) U.S. Cl. ..................... 424/490; 424/489; 424/491; 424/501; 435/455; 435/456; 435/459; 435/320.1
(58) Field of Search ..................... 435/455, 456, 435/459, 320.1; 424/489, 490, 491, 501

(56) References Cited

U.S. PATENT DOCUMENTS 5,578,325 * 11/1996 Domb et al. ..................... 424/501
5,928,647 * 7/1999 Rock ............................. 424/196.11

FOREIGN PATENT DOCUMENTS

| WO96/20698 | 7/1996 | (WO) . |
| WO 97/03702 * | 2/1997 | (WO) . |
| WO97/03702 | 2/1997 | (WO) . |
| WO98/07410 | 2/1998 | (WO) . |
| WO98/56363 | 12/1998 | (WO) . |
| WO98/56370 | 12/1998 | (WO) . |

OTHER PUBLICATIONS

Abdallah et al., *Biol. Cell.*, 1995, 85, 1.
Bazile et al., *Journal of Pharmaceutical Sciences*, 1995, 84, 493.
Chaiet et al., *Arch. Biochem. Biophys.*, 1964, 106, 1.
Cho et al., *Macromol. Rapid Commun.*, 1997, 18, 361.
Cotten et al., *Methods Enzym.*, 1993, 217, 618.
Crotts et al., *J. Microencapsulation*, 1998, 15, 699.
Crystal, R.G., "The Gene as the Drug", *Nature Medicine*, 1995, 1, 15.
Felgner et al., *Adv. Drug Del. Rev.*, 1990, 5, 163.
Green et al., *Av. Protein Chem.*, 1975, 29, 85.
Gref et al., *Science*, 1994, 1600.
Kaplan et al., *Biochim. Biophys. Acta*, 1983, 728, 112.
Kawashima et al., *Eur. J. Pharm. Biopharm.*, 1998, 45, 41.
Langer et al., "New Methods of Drug Delivery", *Science*, 1990, 249, 1527.
Mao et al., "DNA–Chitosan Nanospheres for Gene Delivery" Proceedings of the International Symposium on Controlled Release Bioactive Materials, Jul. 7, 1996, p. 401.
Mathiowitz et al., "Biologically Erodable Microspheres as Potential Oral Drug Delivery Systems", *Nature*, 1997, 386, 410.
Mulligan et al., "The Basic Science of Gene Therapy", *Science*, 1993, 260, 926.
Niwa et al., *Journal of Controlled Release*, 1993, 25, 89.
Peppas et al., "New Challenges in Biomaterials", *Science*, 1994, 263, 1715.
Peracchia et al., *Pharm. Res.*, 1998, 15, 550.
Tobio et al., *Pharm. Res.*, 1998, 15, 270.
Troung et al., "A Target–Specific Microspheres Drug Delivery System made of Enzymatically Degradable Gelatin and Chondroitin Sulfate Coacervates" *Proceedings of the International Symposium on Controlled Release Biomaterials*, vol. 20, Jul. 25, 1993, p. 474.

* cited by examiner

*Primary Examiner*—David Guzo
(74) *Attorney, Agent, or Firm*—Karoline K. M. Shair; Choate, Hall & Stewart

(57) ABSTRACT

The present invention provides biodegradable polymer nanospheres capable of transporting and releasing therapeutic agents, specifically nucleic acids. In preferred embodiments, a sub-150 nm nanosphere is formed containing nucleic acids. Thereafter, the agent is released from the nanosphere. In one embodiment a biodegradable polymer nanosphere surface has attached to it a targeting moiety. In another embodiment, the biodegradable polymer nanosphere surface has attached to it a masking moiety. In yet another embodiment both targeting and masking moieties are attached to the nanosphere surface.

41 Claims, 3 Drawing Sheets

SUB-100NM BIODEGRADABLE POLYMER SPHERES CAPABLE OF TRANSPORTING AND RELEASING NUCLEIC ACIDS

This application claims priority to the co-pending provisional application entitled "Sub-100 nm Biodegradable Polymer Spheres Capable of Transporting and Releasing Nucleic Acids" 60/069,360 filed on Dec. 12, 1997, which is incorporated in its entirety by reference.

GOVERNMENT SUPPORT

This invention was made with government support under Grant Number NIH-5R01-GM26698 awarded by the National Institutes of Health. The government has certain rights in the invention.

BACKGROUND OF THE INVENTION

The recent advances in drug discovery and molecular and pharmaceutical biology have created a need for the development of effective mechanisms for delivering therapeutic agents into cells. In but one example, researchers have particularly struggled to develop efficient means for introducing nucleic acids into cells. For example, in recent years, gene therapy has become a widely-publicized new method of ameliorating disease. However, very few, if any, attempts have successfully proceeded through clinical trials. The main reason lies in the lack of an efficient, targetable in vivo delivery vehicle despite much effort expended in developing viral and non-viral vectors. The development of a method to efficiently introduce nucleic acids into cells would be useful, for example, in gene therapy, antisense therapy, research purposes (e.g., to study cell differentiation, growth and carcinogenic transformation or for the creation of animal models for human disease; see, for example, Abdallah, *Biol. Cell,* 1995, 85, 1, and references therein).

One potential in vivo delivery vehicle is a biodegradable polymer. Specifically, the advantages of a biodegradable polymer gene carrier over existing vectors are the stability and ease of handling of polymer systems, the ease with which one can add different characteristics to the carrier either by polymer design, and the protection they can provide the nucleic acids which they are carrying. Polymers are, relatively speaking, newcomers in this field (see, for example, Felgner, *Adv. Drug Del. Rev.* 1990, 5, 163). There are two ways polymers have been explored as potential vectors: 1) as a capsule or mesh which houses genetically modified cells, or 2) as a nucleic acid carrier itself.

The ability of certain polymer microspheres and nanospheres to release drugs such as small molecules, peptides and proteins, has been previously described in the literature (see, for example, Niwa et al., *J. Controlled Release* 1993, 25, 89; Cho et al., *Macromol. Rapid Commun.,* 1997, 18, 361). In addition to the encapsulation of drugs such as small molecules, peptides and proteins, the formulation of microspheres encapsulating DNA has been described (see, for example, Mathiowitz et al., *Nature,* 1997, 386, 410; and Mathiowitz et al., WO97/03702), and also the preparation of nanospheres small enough to be used in injectable formulations has also been described (see, for example, Gref et al., *Science,* 1994, 1600; Bazile et al., *J. Pharmaceut. Sci.* 1995, 84, 493.). To date, however, there has been no description of the development of a system whereby 1) nanospheres encapsulating nucleic acids are formed and 2) the nucleic acids are subsequently released.

Clearly, however, there remains a need to develop a system in which nucleic acids can be encapsulated in nanospheres, and can also subsequently be released from these nanospheres. Additionally, it would also be desirable to encapsulate nucleic acids in nanospheres having targeting or masking moieties so that nucleic acids could be directly delivered and subsequently released into a specific cellular target.

The present invention for the first time demonstrates that nucleic acids, specifically DNA, can be encapsulated into nanospheres and can also be subsequently released from them. As a result, the present invention accomplishes the first step of development for an injectable system for eventual development into a fully functioning gene delivery vehicle. Clearly, this invention has wide implications for commercial applications such as gene replacement therapy, gene augmentation, or oligonucleotide delivery for antisense applications.

SUMMARY OF THE INVENTION

The present invention discloses a biodegradable polymer nanosphere capable of 1) encapsulating nucleic acids, and 2) releasing nucleic acids over a period of time. Specifically, in one aspect, the invention provides a system for delivering biologically agents, such as nucleic acids, from biodegradable polymer nanospheres, including forming a nanosphere encapsulating the desired agent, and subsequently releasing the agent from the nanosphere over a period of time. In another aspect, the present invention provides a method for delivering and releasing nucleic acids to cells including 1) encapsulating the desired agent within the nanosphere, 2) contacting the desired cells with the nanosphere encapsulating the nucleic acids, whereby release of the nucleic acids into the desired target is effected over a period of time. In a preferred embodiment, to effect the delivery of nucleic acids to specific cells, a targeting moiety is attached to the surface of the nanospheres. In another preferred embodiment, to effect the intravenous delivery of nucleic acids, a masking moiety is attached to the surface of the nanospheres. In yet another preferred embodiment, a system is provided for the intravenous delivery of nucleic acids by attaching both a masking and targeting moiety to the surface of the nanospheres.

DETAILED DESCRIPTION OF THE INVENTION

Figure 1:
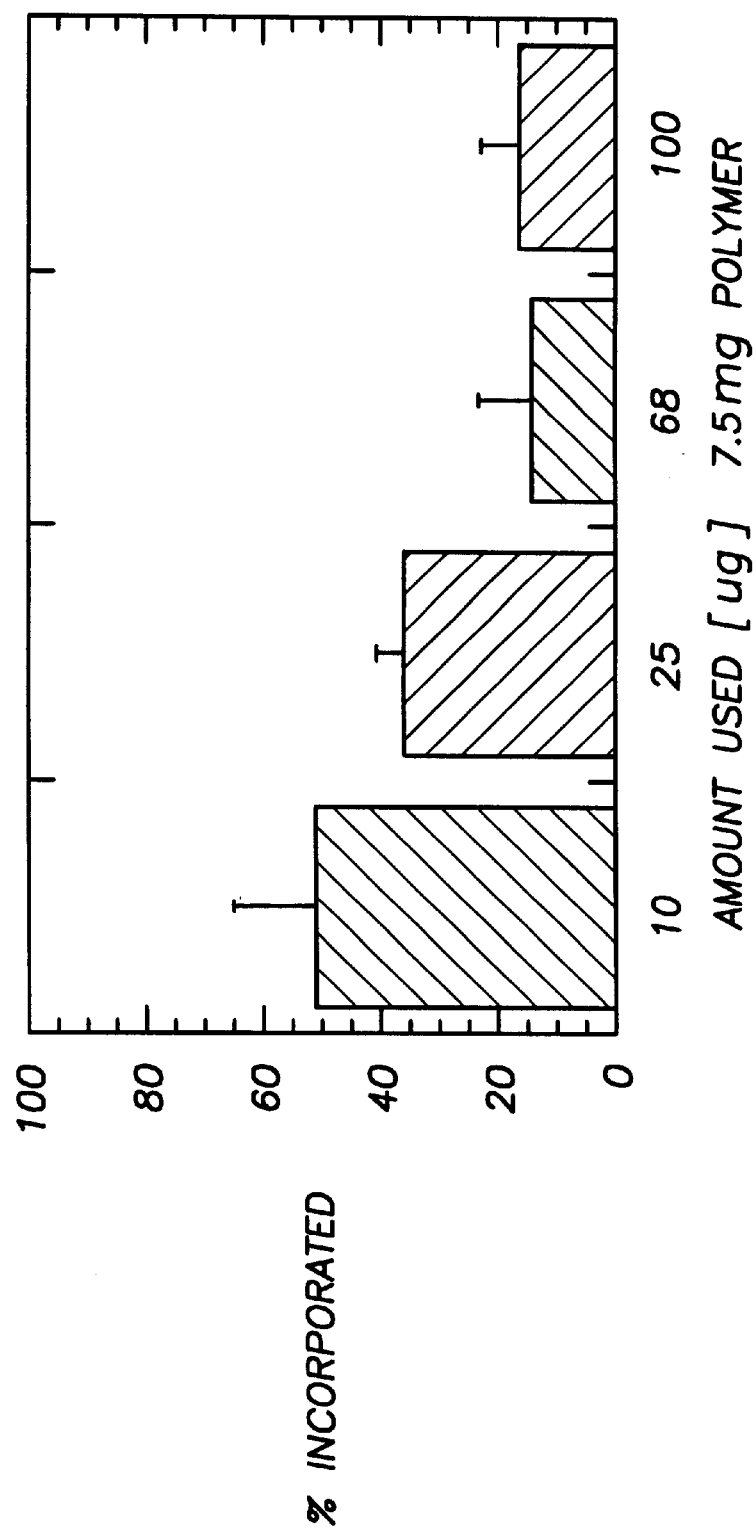
FIG. 1 is a graph which depicts the percent incorporation of $^{32}$P labeled plasmid DNA in PLGA nanospheres when the amount of plasmid is varied.

Recognizing the importance of the development of systems that are effective not only at encapsulating biological agents such as nucleic acids, but that are also able to release these biological agents controllably, the present invention provides a system for the delivery of nucleic acids comprising: 1) encapsulating nucleic acids in biodegradable polymers and 2) releasing these encapsulated nucleic acids from the biodegradable polymers. The present invention also provides a method for the delivery of nucleic acids to cells comprising 1) formation of a nanosphere encapsulating nucleic acids and 2) contacting the nanospheres encapsulating the nucleic acids with cells, whereby the encapsulated nucleic acids are released from the nanospheres.

In general, the delivery agent is comprised of a biodegradable polymer, a condensation agent, and a desired therapeutic agent, most preferably nucleic acids, that are formulated as a nucleic acid encapsulating nanosphere. In preferred embodiments, these nanospheres are formulated as sub-150 nm spheres of which at least 50% of the size distribution of nanospheres is sub-100 nm. In particularly preferred embodiments, the nanospheres are all sub-100 nm. In particularly preferred embodiments, the nanosphere compositions utilized in the inventive method have attached to the surface a masking moiety, a targeting moiety, or alternatively a masking moiety and a targeting moiety.

Various characteristics of the inventive compositions utilized in preferred embodiments of the present invention are discussed in more detail below; certain examples of inventive compositions for use in the method of the present invention are also presented.

Delivery and Release Compositions and Systems

As mentioned above, the method for delivery and release of a therapeutic agent of the present invention comprises 1) the formation of a nucleic acid encapsulating nanosphere, comprised of a biodegradable polymer, an encapsulating component and a desired therapeutic agent, and 2) controlled release of the therapeutic agent from the inventive composition. In general, formation of the nucleic acid encapsulating nanospheres comprises dissolving a biodegradable polymer in a solvent with a condensation agent and a therapeutic agent, and subsequent precipitation. The removal of the solvent then yields the nucleic acid encapsulating nanospheres. The precipitation/solvent evaporation method is preferred for the formulation of the nanosphere composition because this method allows for the encapsulation of drug molecules, especially shear-sensitive molecules such as DNA, without exposing the molecules to undue mechanical stress or harsh chemical processing. One of ordinary skill in the art will appreciate that a variety of polymers, condensation agents, and therapeutic agents can be used in the formation of the inventive composition. For example, polymers that can be utilized include, but are not limited to, poly (e-caprolactone) and poly (hydroxybutyrate) and poly (orthoesters). Condensing agents include, but are not limited to, poly(l-lysine), poly (d-lysine), spermine, spermidine, poly (lactic acid-co-lysine), dendrimers, 1,2-diacyl-3-trimethylammonium-propane (TAP) and 1,2-diacyl-3-dimethylammonium-propane (DAP), dimethyldioctadecylammonium bromide (DDAB), and other cationic lipids. In particularly preferred embodiments, the therapeutic to be delivered is a nucleic acid, however, one of ordinary skill in the art will realize that a variety of therapeutic agents can be utilized, including but not limited to, lipophilic drugs, biomolecules, and small organic molecules.

In particularly preferred embodiments, the therapeutic agent utilized in the formation of the composition is a nucleic acid (Example 1), and the polymer spheres formulated are sub-150 nm, of which 50–100% of the distribution is sub-100 nm. In most preferred embodiments, all of the polymer spheres formulated are sub-100 nm.

In but one example, the method of encapsulation includes dissolving a polymer such as poly(oactic-co-glycolic acid) in an appropriate solvent such as 2,2,2-trifluoroethanol (TFE) in the presence of a condensing agent, such as a cationic lipid, and a therapeutic agent. It will be appreciated that different polymer concentrations, preferably 2.5 to 7.5 mg/ml, more preferably lower concentrations and most preferably about 2.5 mg/ml, can be used. Additionally, it will be appreciated that a variety of compatible solvents can be utilized as will be readily determined by one of ordinary skill in the art. Furthermore, a range of 0 to 100% ethanol, or other similar non-solvents, or precipitation agents, as will be readily discernable to one of ordinary skill in the art, can be used in the process as a precipitation agent. The solvent:non-solvent ratio can be varied from 1~2.5. DNA concentrations are preferably in the range of 0.1 to 1 mg/ml, more preferably from 0.25 to 0.68, and most preferably about 0.68 mg/ml. Finally, the nanospheres can be formed under conditions where positive:negative charge ratios of condensing agent:nucleic acid were varied preferably from 1 to 1000, more preferably from 25 to 100 and most preferably about 25. This system affords a method for preparing nanospheres of different sizes, including those less than 100 nm.

In a preferred embodiment of the present invention, targeting moieties are attached to the surface of the nanospheres. As discussed previously, such small nanospheres have the potential to be targeted to specific cells in vivo and to be taken up by receptor-mediated endocytosis. The targeting moieties can be selected by one of ordinary skill in the art keeping in mind the specific cell surface to be targeted. For example, if one wishes to target the asialoglycoprotein receptor on the hepatocytes in the liver, an appropriate targeting moiety would be clustered trigalactosamine. Once a specific targeting moiety has been selected for a particular cell to target, the different targeting moieties can be attached either by covalent linkage directly onto the particle surface, or by indirect linkage via, for example, a biotin-avidin bridge. More specifically, in one embodiment, avidin is attached covalently to the polymer and a biotinylated ligand attaches non-covalently to the avidin. In another embodiment, biotin is covalently attached to the polymer, and then avidin is used as a bridge between the biotinylated polymer and the biotinylated ligand. Preferred targeting agents are biocompounds, or portions thereof, that interact specifically with individual cells, small groups of cells, or large categories of cells. Examples of useful targeting agents include, but are in no way limited to, low-density lipoproteins (LDS's), transferrin, asiaglycoproteins, gp120 envelope protein of the human immunodeficiency virus (HIV), and diptheria toxin, antibodies, and carbohydrates. A variety of agents that direct compositions to particular cells are known in the art (see, for example, Cotten et al., *Methods Enzym*, 1993, 217, 618).

In another embodiment of the presently claimed invention, masking moieties are attached to the surface of the nanospheres. These masking moieties prevent the recognition by a specific cell surface and instead allows for intravenous administration applications. For example, the surface masking characteristics are provided by poly (ethylene glycol) (PEG) by using various PEG-PLA and PLGA mixtures in the initial polymer solution. (Example 4). It will be appreciated by those skilled in the art that other masking moieties can also be employed for use in the presently claimed invention. As mentioned earlier, both targeting and surface masking (for example oligosaccharides and other surfactants) moieties may be attached or adsorbed to the surface of the nanospheres. When both targeting and masking moieties are utilized, some optimization must be done in order to obtain enough of a specificity for a specific target cell but to retain enough of the masking capacity to avoid non-specific uptake in vivo. Other means can be co-employed to achieve cell specificity. Such means can be directly programmed into the nucleic acids themselves, such as using the albumin promoter for targeting hepatocytes.

Figure 2:
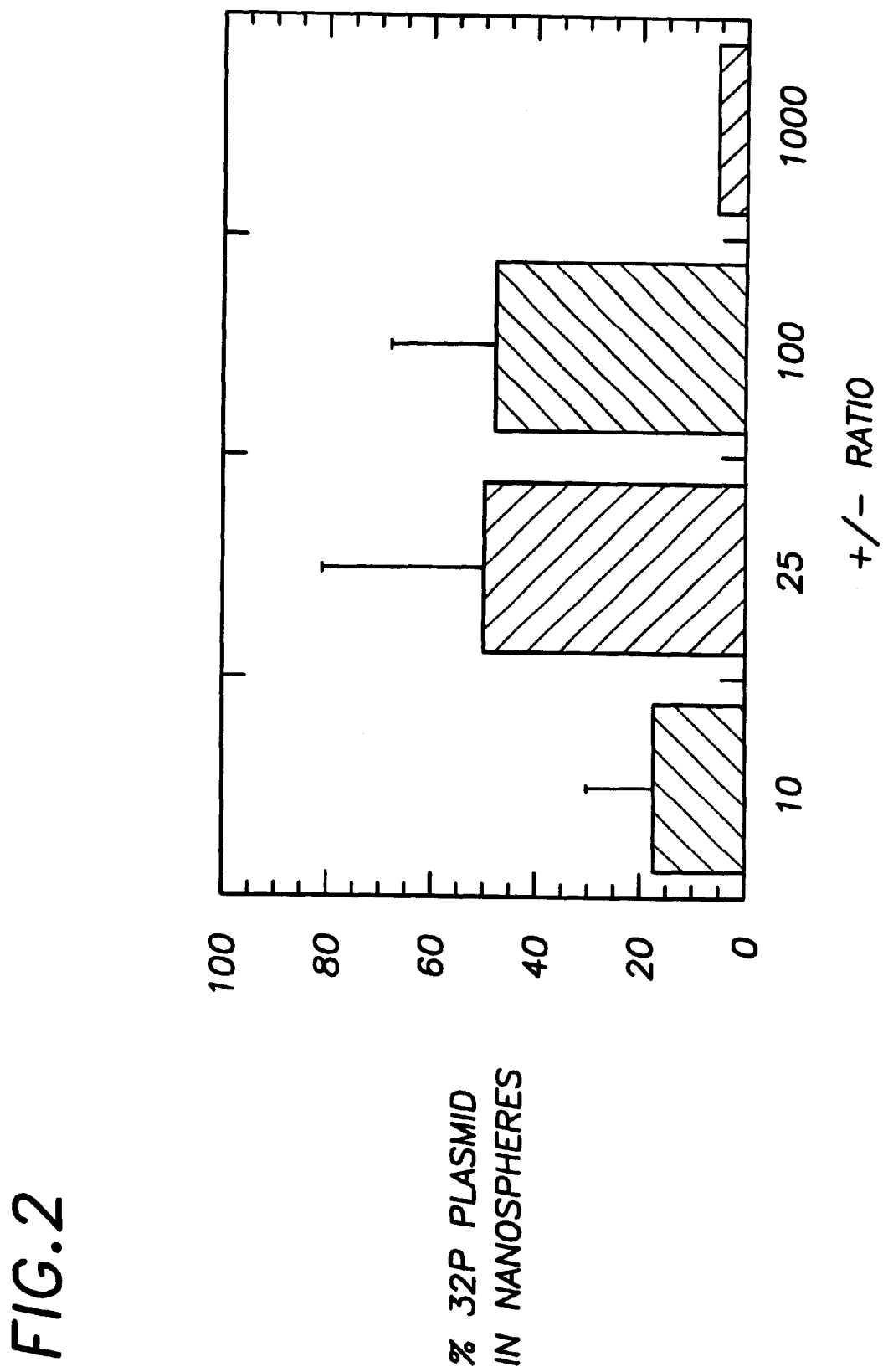
FIG. 2 is a graph which depicts the % incorporation of $^{32}$P labeled DNA in nanospheres changing the +/− ratio.

Once the desired compositions have been prepared, the particle size and polydispersity of the nanospheres can be measured using quasi-elastic light scattering, and the particle size confirmed by transmission electron microscopy, as discussed in Example 2. The loading efficiency of the nucleic acid into these nanospheres has been shown to be 30–60% and can be determined using radiolabeled plasmid nanospheres as described in Example 3. The percentage of $^{32}P$ labeled plasmid DNA into PLGA nanospheres is shown in FIG. 1. Additionally, FIG. 2 depicts the incorporation of $^{32}P$ labeled DNA in nanospheres changing the +:− ratio by changing the amount of cationic lipid: DNA, and shows the greatest incorporation when the ratio is in the range of 25 to 100.

Figure 3:
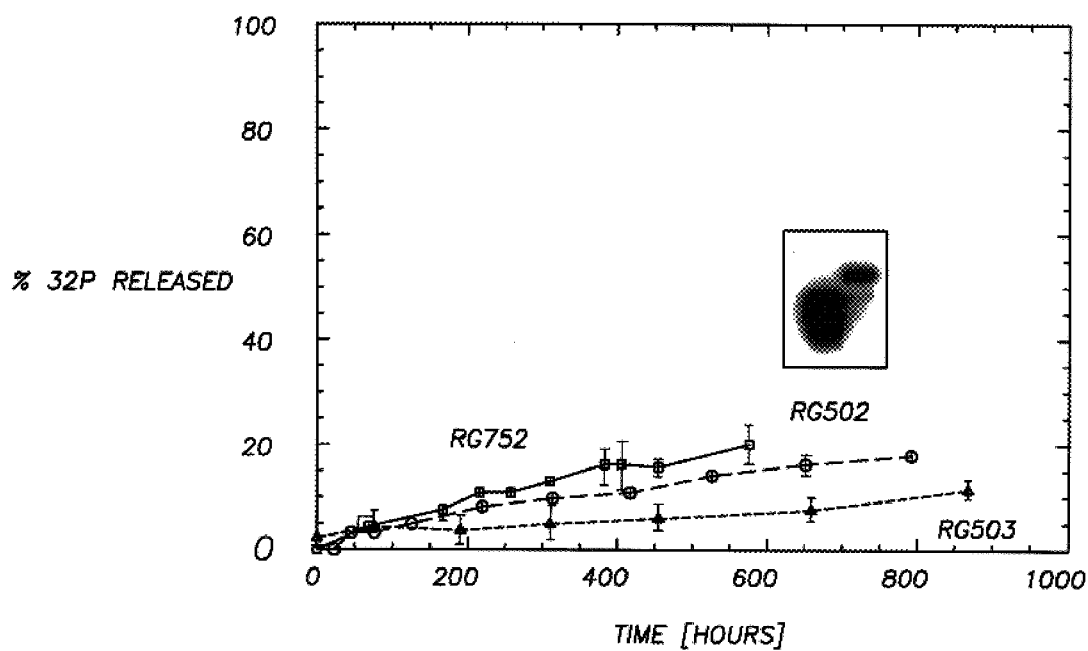
FIG. 3 is a plot which depicts the free DNA released from polymer nanospheres where RG 752, 502, 503 are polymers of different $M_w$ and lactic:glycolic acid ratios from Boehringer Ingelheim (Ingelheim, Germany).

As discussed previously, the system of the present invention ultimately provides for the release of the therapeutic agent, preferably nucleic acids, from these nanospheres. In an exemplary embodiment, the release of the plasmid DNA occurs preferably over 200 hours or alternatively so that there is not a burst that would release DNA prior to the nanosphere's arrival at a particular target, such as a cell. FIG. 3 reveals the amount of free DNA released from the above mentioned art of nanosphere formation. These spheres release at a constant rate for a long time despite the initial expectation of instant release of therapeutic reagents from such small spheres with such a high surface area: volume ratio. These spheres can potentially be made to release at different rates as desired. The inset autoradiograph shows a band of original linear DNA on the left lane with a sample at greater than 600 hours. The higher molecular weight bands are the DNA complexed to the spheres, unable to penetrate the agarose gel.

Uses

Those of ordinary skill in the art will immediately appreciate that the present invention can be utilized in a wide variety of applications to deliver agents into cells. A few particularly preferred applications are discussed in more detail here in order to highlight some of the characteristics and advantages of the inventive systems.

As discussed at length above, the present invention is particularly well adapted for delivery of nucleic acids into cells. As such, the inventive compositions are useful for various applications including gene therapy and antisense regulation. To give but a few examples of particular embodiments of nucleic acid delivery applications of the present invention, inventive compositions can be employed to introduce a gene into specific cells or tissue that will express the protein encoded by that gene and thereby correct a defect caused by a deficiency in that gene in the cells or tissue. Alternatively, inventive compositions can also be used to turn off the function of a specific gene, for example an oncogene in a tumor cell, by delivering antisense messenger RNA into a cell that will bind with the sense messenger RNA so that translation of the message and therefore expression of the protein encoded by that message will not occur.

Inventive compositions can be used in therapeutic gene delivery applications, for example to introduce "suicide genes" into cancer cells that will turn on the cell death pathway. Drug sensitivity genes can also be introduced into tumor cells. For example, cells can be genetically engineered to express prodrug activating enzyme, such as herpes simplex virus thymidine kinase, which phosphorylates ganciclovir creating toxic metabolites that kill tumor cells upon exposure to prodrug.

In the arena of immunotherapy, inventive compositions can be employed in "adoptive immunotherapy" preparations, in which genetically engineered tumor-infiltrating lymphocytes are prepared that express tumor necrosis factor and can be used to treat patients with melanoma. Immunomodulation of tumor cells to invoke an immune response directed toward specific target cell population is yet another area to which this invention can be applied.

The presently claimed invention may be demonstrated by the following examples, but are not limited to these particular embodiments.

EXAMPLE 1

Preparation of DNA-Loaded Nanospheres

Nanospheres containing plasmid DNA are made by the precipitation/solvent evaporation method. This method allows the encapsulation of drug molecules, especially shear-sensitive molecules such as DNA, without exposing the molecules to undue mechanical stress or harsh chemical processing. In one formulation of DNA-loaded nanospheres, the fabrication procedure is as follows: PLGA 75:25 is dissolved in TFE at 2.5 mg/ml. The condensing agent DDAB is also dissolved in TFE separately at 10 mg/ml. Plasmid DNA is harvested from *E.coli* (strain DH5alpha) using a modified cesium chloride isolation procedure and suspended in water at 1 mg/ml. Initially, 200 µl of the lipid solution is poured into 3 ml of the polymer solution. One hundred microliters of the DNA solution is slowly introduced into the TFE solution by gentle pipetting. Then, 5 ml of 50% ethanol is poured into the polymer/lipid/DNA mixture and mixed by inversion to form an instant nanosuspension of DNA-loaded spheres. The entire mixture is then poured into 10 ml of water and the solvent is removed by rotary evaporation (Buechi, Rotavapor R110, ZH, Switzerland) at 37° C., and high vacuum conditions 20 mm Hg. Nanospheres can be made from PLGA, poly (e-caprolactone) and poly (hydroxybutyrate) and poly (orthoesters). The particles can be formed at different polymer concentrations (2.5 to 7.5 mg/ml) as well as different ethanol concentrations (0 to 100%). Nanospheres were formed under conditions where positive:negative charge ratios were varied from 1–1000 and also DNA concentrations, from 0.1 to 1 mg/ml. Some other condensing agents tried are poly (l-lysine), poly (d-lysine), spermine, spermidine, poly (lactic acid-co-lysine), dendrimers, 1,2-diacyl-3-trimethylammonium-propane (TAP) and 1,2-diacyl-3-dimethylammonium-propane (DAP) and other cationic lipids.

EXAMPLE 2

Particle Size Analysis

Particle size and polydispersity were measured using quasi-elastic light scattering (Brookhaven Documents, Holtsville, N.Y.). The particle size was also confirmed by transmission electron microscopy (JEOL 1200CX, Tokyo, Japan). Samples were placed on carbon-coated copper grids and stained with 4% uranyl acetate.

EXAMPLE 3

DNA Loading Determination and Release Studies

Plasmid DNA was linearized with an appropriate restriction enzyme (for pCMV-bgal, EcoRI was used from New England Biolabs, Beverly, Mass.). The linear DNA was then 3' end labeled with [α-$^{32}P$] DATP (Amersham Life Sciences, Arlington Heights, Ill.) by Kienow fill-in (Klenow fragment, New England Biolabs). Excess radionucleotides were removed by Spin Columns (Sigma, St. Louis, Mo.). DNA loading was determined by making nanospheres as described above with radiolabeled plasmid. Free DNA and lipid:DNA complexes were separated from the nanospheres by sucrose gradient centrifugation (Sorvall RC70, DuPont, Wilmington, Del.) and the radioactivity from the appropriate fraction was counted (Packard 2000CA, Packard Downers, Inc., Grove, Ill.). The loading efficiency was determined by the ratio of counts in the sample nanosphere fraction versus the pre-separated sample multiplied by 100%. Release studies were conducted from similarly isolated polymer nanospheres after the sucrose concentration was diluted to 5% using Centriprep 500 (Amicon, Beverly, Mass.). Release samples were taken at appropriate time intervals and ultracentrifuged to remove particles from free DNA. The supernatant was counted to determine the radioactivity released from the spheres. The mass of DNA was determined given the counts and the specific activity of labeled plasmid.

EXAMPLE 4

Method for Attaching Surface-Masking and/or Targeting Moieties

Surface masking characteristics are provided by PEG on the nanospheres by using various PEG-PLA and PLGA mixtures in the initial polymer solution. Non-covalent attachment of targeting moieties is achieved by incubating biotin-PEG-PLA: PLGA nanospheres with excess streptavidin or avidin, in turn, incubating the avidinylated spheres with biotin-ligand. Covalent attachment methods use activated esters (N-hydroxysuccinimidyl esters) on PEG-PLA with which amine groups from desirable ligands can be reacted.

What we claim is:

1. A method for the delivery of nucleic acids comprising:
   forming nucleic acid containing nanospheres, wherein said nanospheres are sub-150 nm polymer spheres of which at least 50% of the size distribution of nanospheres is sub-100 nm; and
   releasing said nucleic acids from said nanospheres over a period of time.

2. The method of claim 1, wherein all of said nanospheres are sub-100 nm.

3. A method for the delivery of nucleic acids to specific cells comprising:
   forming nucleic acid containing nanospheres, wherein said nanospheres are sub-150 nm polymer spheres, of which at least 50% of the size distribution of nanospheres is sub-100 nm, and wherein a targeting moiety is attached to the surface of said nanospheres; and
   releasing said nucleic acids from said nanospheres over a period of time.

4. The method of claim 3, wherein all of said nanospheres are sub-100 nm.

5. The method of claim 3, wherein said targeting agent is selected from the group consisting of low-density lipoproteins, transferrin, asiaglycoproteins, gp120 envelope protein of the human immunodeficiency virus (HIV), diptheria toxin, antibodies, trigalactosamine, and carbohydrates.

6. The method of claim 3, wherein said targeting moiety is attached by a covalent linkage.

7. The method of claim 3, wherein said targeting moiety is attached by an indirect linkage.

8. A method for the intravenous delivery of nucleic acids comprising:
   forming nucleic acid containing nanospheres, wherein said nanospheres are sub-150 nm polymer spheres of which at least 50% of the size distribution of nanospheres is sub-100 nm, and wherein a masking moiety is attached to the surface of said nanospheres; and
   releasing said nucleic acids from said nanospheres over a period of time.

9. The method of claim 8, wherein all of said nanospheres are sub 100 nm.

10. The method of claim 8, wherein said surface masking moiety is poly(ethylene glycol).

11. A method for the intravenous delivery of nucleic acids comprising:
    forming nucleic acid containing nanospheres, wherein said nanospheres are sub-150 nm polymer spheres of which at least 50% of the size distribution of nanospheres is sub-100 nm, and wherein a targeting moiety and a masking moiety is attached to the surface of said nanospheres; and
    releasing said nucleic acids from said nanospheres.

12. The method of claim 11, wherein all of said nanospheres are sub-100 nm.

13. The method of claim 11, wherein said targeting agent is selected from the group consisting of low-density lipoproteins, transferrin, asiaglycoproteins, gp120 envelope protein of the human immunodeficiency virus (HIV), diptheria toxin, antibodies, trigalactosamine, and carbohydrates.

14. The method of claim 11, wherein said targeting moiety is attached by a covalent linkage.

15. The method of claim 11, wherein said targeting moiety is attached by an indirect linkage.

16. The method of claim 11, wherein said surface masking moiety is poly(ethylene glycol).

17. A system for the delivery of nucleic acids comprising:
    nanospheres containing nucleic acids, wherein said nanospheres are sub-150 nm polymer spheres of which at least 50% of the size distribution of spheres is sub-100 nm,
    whereby said nucleic acids are controllably released from said nanospheres.

18. The system of claim 17, wherein all of said nanospheres are sub-100 nm.

19. A system for the biocompatible transport and release of nucleic acids comprising:
    nanospheres containing nucleic acids, wherein said nanospheres containing nucleic acids are sub-150 nm polymer spheres of which at least 50% of the size distribution of spheres is sub-100 nm, and wherein a targeting moiety is attached to the surface of said nanospheres,
    whereby said nucleic acids are controllably released from said nanospheres.

20. The system of claim 19, wherein all of said nanospheres are sub-100 nm.

21. The system of claim 19, wherein said targeting agent is selected from the group consisting of low-density lipoproteins, transferrin, asiaglycoproteins, gp120 envelope protein of the human immunodeficiency virus (HIV), diptheria toxin, antibodies, trigalactosamine, and carbohydrates.

22. The system of claim 19, wherein said targeting moiety is attached by a covalent linkage.

23. The system of claim 19, wherein said targeting moiety is attached by an indirect linkage.

24. A system for the intravenous delivery of nucleic acids comprising:
    nanospheres containing nucleic acids, wherein said nanospheres containing nucleic acids are sub-150 nm polymer spheres of which at least 50% of the size distribution of spheres is sub-100 nm, and wherein a surface masking moiety is attached to the surface of said nanospheres, whereby said nucleic acids are controllably released from said nanospheres.

25. The system of claim 24, wherein all of said nanospheres are sub-100 nm.

26. The system of claim 24, wherein said surface masking moiety is poly(ethylene glycol).

27. A system for the intravenous delivery of nucleic acids comprising:

nanospheres containing nucleic acids, wherein said nanospheres containing nucleic acids are sub-150 nm polymer spheres of which at least 50% of the size distribution of spheres is sub-100 nm, and wherein both a targeting moiety and a surface masking moiety are attached to the surface of said nanospheres, whereby said nucleic acids are controllably released from said nanospheres.

28. The system of claim 27, wherein all of said nanospheres are sub-100 nm.

29. The system of claim 27, wherein said targeting agent is selected from the group consisting of low-density lipoproteins, transferrin, asiaglycoproteins, gp120 envelope protein of the human immunodeficiency virus (HIV), diptheria toxin, antibodies, trigalactosamine, and carbohydrates.

30. The system of claim 27, wherein said targeting agent is attached by a covalent linkage.

31. The system of claim 27, wherein said targeting agent is attached by an indirect linkage.

32. The system of claim 27, wherein said surface masking moiety is poly(ethylene glycol).

33. A method for introducing nucleic acids into cells or subcellular components comprising the steps of:

encapsulating nucleic acids within nanospheres, wherein said nanospheres encapsulating nucleic acids are sub-150 nm polymer spheres of which at least 50% of the size distribution of spheres is sub-100 nm; and contacting said nanospheres encapsulating nucleic acids with cells, whereby said encapsulated nucleic acids are released from said nanospheres.

34. The method of claim 33, wherein all of said nanospheres are sub-100 nm.

35. The method of claim 33, wherein said nanospheres containing nucleic acids have a targeting moiety attached to the surface of said nanospheres.

36. The method of claim 33, wherein said nanospheres containing nucleic acids have a surface masking moiety attached to the surface of said nanospheres.

37. The method of claim 33, wherein said nanospheres containing nucleic acids have both a targeting moiety and a surface masking moiety attached to the surface of said nanospheres.

38. The method of claim 35 or 37, wherein said targeting agent is selected from the group consisting of low-density lipoproteins, transferrin, asiaglycoproteins, gp120 envelope protein of the human immunodeficiency virus (HIV), diptheria toxin, antibodies, trigalactosamine, and carbohydrates.

39. The method of claim 35 or 37, wherein said targeting moiety is attached by a covalent linkage.

40. The method of claim 35 or 37, wherein said targeting moiety is attached by an indirect linkage.

41. The method of claim 36 or 37, wherein said surface masking moiety is poly(ethylene glycol).

* * * * *